(12) United States Patent
Orenga

(10) Patent No.: US 6,921,635 B1
(45) Date of Patent: Jul. 26, 2005

(54) **CULTURE AND IDENTIFICATION MEDIA SPECIFIC OF DIFFERENT SPECIES OF *CANDIDA* AND ANALYSIS METHODS**

(75) Inventor: Sylvain Orenga, Saint-Andre (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/486,037

(22) PCT Filed: Jul. 31, 1998

(86) PCT No.: PCT/FR98/01717

§ 371 (c)(1),
(2), (4) Date: Feb. 18, 2000

(87) PCT Pub. No.: WO99/09207

PCT Pub. Date: Feb. 25, 1999

(30) Foreign Application Priority Data

Aug. 20, 1997 (FR) .............................. 97 10635
Apr. 20, 1998 (FR) ............................. 98 05269

(51) Int. Cl.[7] ............................ C12Q 1/00; C12Q 1/04; C12Q 1/24; C12Q 1/34; C12Q 1/54
(52) U.S. Cl. ............................. 435/4; 435/14; 435/18; 435/30; 435/34
(58) Field of Search ................................ 435/4, 14, 18, 435/30, 34

(56) References Cited

U.S. PATENT DOCUMENTS

| | | | |
|---|---|---|---|
| 4,874,695 A | * | 10/1989 | Pincus |
| 5,120,718 A | | 6/1992 | Goldman et al. |
| 5,272,072 A | * | 12/1993 | Kaneko et al. |
| 5,534,415 A | * | 7/1996 | Orenga |
| 2002/0137176 A1 | * | 9/2002 | Wong-Madden |

FOREIGN PATENT DOCUMENTS

FR    2 659 982    9/1991

OTHER PUBLICATIONS

Mega et al (J. Biochem. vol. 71, pp 107–114, 1972).*
Bendel et al. XP–002064132 "Distinct Mechanisms of Epithelial Adhesion for *Candida albicans* and *Candida tropicalis*" vol. 92, Oct. 1993, pp. 1840–1849.
Mira–Gutierrez et al., XP–002064133 "Identification of yeasts by hydrolysis of amides" Nov. 8, 1994, pp. 101–106.
Crist, Jr. et al., XP–002064134 "Comparison of the MUREX C. Albicans, Albicans/Sure, and Bacticard *Candida* Test Kits with the Germ Tube Test for Presumptive identification of *Candida albicans*" vol. 36, Jul. 5, 1996, pp. 2616–2618.
Heelan et al., XP–002064135 "Comparison of Rapid Testing Methods for Enzyme Production with the Germ Tube Method of Presumptive Identification of *Candida albicans*" vol. 34, No. 11 Aug. 1996, pp. 2847–2849.
Garcia–Martos et al., XP–002064136 "Contribution to the knowledge of the enzymatic activity of yeasts of clinical interest" Jul. 1995, pp. 9–13.

* cited by examiner

*Primary Examiner*—Mark Navarro
(74) *Attorney, Agent, or Firm*—Oliff & Berridge, PLC

(57) ABSTRACT

The invention concerns a culture and identification medium specific of yeasts comprising a chromogenous or fluorigenous substrate, capable of being hydrolyzed by an enzyme of the hexosaminidase and optionally glucosidase group, and/or at least a compound selectively inhibiting the hexosaminidase activity of *C. tropicalis*, and a method for selectively identifying *C. albicans* and/or *C. tropicalis* and/ or other *Candida*, using such a medium. The invention is particularly applicable in the biomedical field and more particularly in bacteriology.

20 Claims, No Drawings

CULTURE AND IDENTIFICATION MEDIA SPECIFIC OF DIFFERENT SPECIES OF *CANDIDA* AND ANALYSIS METHODS

The present invention relates to a medium for the culturing and specific identification of yeasts and to a microbiological analysis process to specifically identify *Candida albicans* and *Candida tropicalis* yeasts and/or to differentiate *C. albicans* and *C. tropicalis* yeasts.

The *C. albicans* species is the one most commonly isolated from clinical samples and gives rise to more or less extensive infections of the skin, the nails and mucous membranes in individuals with normal immune defenses and very serious infections in weakened individuals, and in particular those infected with the Human Immunodeficiency Virus (HIV). According to studies, *C. tropicalis* is the second or third most common species isolated in samples of human origin. It is thus essential not only to be able very rapidly to detect the presence of these yeasts in samples, but also to differentiate those belonging to the *C. albicans* species and those belonging to the *C. tropicalis* species.

To do this, numerous techniques have been proposed in recent years for rapidly identifying *C. albicans* yeasts. Most of these techniques are based on the demonstration of hexosaminidase activity, i.e. of enzymes with N-acetyl-β-D-glucosaminidase or N-acetyl-β-D-galactosaminidase or N-acetyl-β-D-mannosaminidase activity (FR-2 684 110, FR-2 659 982). However, these processes suffer from reduced specificity with respect to yeasts of the *C. tropicalis* species.

The inventors of the present invention have discovered that by inhibiting an enzymatic activity of the *C. tropicalis* species, in particular the hexosaminidase activity, it is possible to overcome the drawbacks of the abovementioned tests and thus to provide a quick and inexpensive means for identifying and/or differentiating yeasts, in particular *C. albicans* and *C. tropicalis*.

Moreover, the glucosidase enzymatic activity has already been the subject of research in certain documents, such as Casal, M. and Linares, M. J. "Contribution to the study of the enzymatic profiles of yeast organisms with medical interest" Mycopathology 81, 155–159 (1983). This activity is positive in a number of strains of *C. albicans*, *C. tropicalis* and *Candida pseudotropicalis* (nowadays known as *Candida kefyr*), but negative for other *Candida* species, for example *C. parapsilosis*, *C. guilliermondii* and *C. krusei*.

It thus appeared to be advantageous to attempt to cumulate, in the same medium, the possibility of investigating two different enzymatic activities, i.e. hexosaminidase and glucosidase activities. Now, it is found that, in the media according to the invention, this cumulation makes it possible to differentiate more specifically *C. albicans* from *C. guilliermondii*, *C. kefyr*, *C. lusitaniae* and/or *C. tropicalis* and from other *Candida* species, but also to differentiate *C. guilliermondii*, *C. kefyr*, *C. lusitaniae* and/or *C. tropicalis* from other *Candida* species.

Needless to say, it is envisaged to combine, in the same medium, an inhibitor according to the invention, and even an activator of hexosaminidase activity, with the substrates specific for the hexosaminidase and glucosidase activities.

The subject of the invention is thus a medium for the culturing and the specific identification of yeasts, comprising a chromogenic or fluorigenic substrate which can be hydrolyzed by an enzyme of the hexosaminidase family, characterized in that the medium also comprises at least one compound which selectively inhibits the hexosaminidase activity of *Candida tropicalis*.

By virtue of the invention, the culture medium especially allows the specific identification of yeasts of the *C. albicans* and/or *C. tropicalis* species.

According to one preferred embodiment of the invention, the culture medium comprises, as selective inhibitor compound, an amide of formula (I):

$$R-(CO-NR'R'')_n \qquad (I)$$

in which, firstly, either R, R' and R", independently of each other, consist of:

a hydrogen atom, a saturated or unsaturated, aliphatic or cyclic hydrocarbon-based chain optionally comprising at least one hetero atom, or each of the radicals R and/or R' and/or R" together form a cyclic, saturated or unsaturated hydrocarbon-based chain optionally comprising at least one hetero atom, and, secondly, n is an integer greater than or equal to 1.

According to the invention, the expression "hydrocarbon-based chain "comprising" at least one hetero atom" means that the hydrocarbon-based chain can be substituted with at least one substituent such as, in particular, —NH$_2$, —COOH, —SH and a halogen atom, and/or can be interrupted with at least one hetero atom such as, in particular, O, S and N.

According to one preferred embodiment of the invention, the culture medium comprises, as selective inhibitor compound, an amide of formula (I):

$$R-(CO-NR'R'')_n \qquad (I)$$

in which, firstly, either R, R' and R", independently of each other, consist of:

a hydrogen atom, a saturated or unsaturated, aliphatic or cyclic hydrocarbon-based chain optionally interrupted by at least one hetero atom, or each of the radicals R and/or R' and/or R" together form a cyclic, saturated or unsaturated hydrocarbon-based chain optionally comprising at least one hetero atom, and, secondly, n is an integer greater than or equal to 1.

According to another preferred embodiment of the invention, the culture medium comprises, as selective inhibitor compound, an amide of formula (I):

$$R-(CO-NR'R'')_n \qquad (I)$$

in which, firstly, R, R' and R", independently of each other, consist of:

a hydrogen atom, an aliphatic hydrocarbon-based chain, and, secondly, n is equal to 1 or 2.

According to a very preferred embodiment of the invention the selective inhibitor compound is an acetamide.

According to another embodiment of the invention, the culture medium comprises an activator which is specific for the hexosaminidase enzyme of *C. albicans*.

According to one preferred embodiment of the invention, the activator which is specific for the hexosaminidase enzyme is N-acetylglucosamine.

According to another embodiment of the invention, the culture medium comprises a mixture of selective inhibitor compounds.

According to one preferred embodiment of the invention, the mixture of selective inhibitor compounds consists of acetamide and formamide.

According to one preferred embodiment of the invention, the medium is liquid or gelled.

According to one embodiment of the invention, the culture medium is gelled and comprises, per liter:

| | |
|---|---|
| peptones or a mixture of peptones | 0.01–40 g |
| yeast extract | 0.01–40 g |
| glucose (source of carbon) | 0–10 g |
| phosphate buffer (pH between 5 and 8.5) | 2.5–100 mM |
| 5-bromo-4-chloro-3-indolyl-N-acetyl-β-D-glucosaminide | 20–600 × $10^{-6}$ M |
| acetamide | 0.01–20 g |
| bacterial inhibitor | 0–20 g |
| agar | 11–20 g. |

According to another preferred embodiment of the invention, the gelled or liquid culture medium described above furthermore comprises N-acetyl-glucosamine at a concentration of 1.0 g/l.

According to another preferred embodiment of the invention, the gelled or liquid culture medium described above furthermore comprises formamide at a concentration of 0.5 g/l.

Another subject of the invention is a micro-biological analysis process for selectively identifying C. albicans and/or C. tropicalis yeasts and/or for differentiating C. albicans and C. tropicalis yeasts, characterized in that the sample to be analyzed is placed directly in contact with at least one identification medium described above.

To this end, the present invention also relates to a medium for detecting and specifically identifying yeasts, which is characterized in that it comprises two substrates, a first chromogenic or fluorigenic substrate which can be hydrolyzed by an enzyme from the hexosaminidase family, and a second chromogenic or fluorigenic substrate which can be hydrolyzed by an enzyme from the glucosidase family.

According to one preferred embodiment of the invention, in this medium, each substrate consists of a specific portion of the enzyme and of a marker portion, characterized in that the marker portion of the first substrate is different from the marker portion of the second substrate.

According to another preferred embodiment of the invention, the medium comprises a hexosaminidase activator and/or inhibitor.

When there is an activator and/or an inhibitor, this activator consists of a hexosamine and/or a hexosaminidine and this inhibitor takes the characteristics described above.

According to yet another preferred embodiment of the invention, the hexosaminidinase substrate consists of an indoxyl derivative and/or the glucosidase substrate consists of an indoxyl derivative.

In all cases, the medium is liquid or gelled.

The present invention also relates to a microbiological analysis process for detecting and selectively identifying certain species of Candida yeasts, which is characterized in that the sample is placed in direct contact with a medium according to either of claims 13 and 18, time is allowed for colorations to appear in the medium, and identification is made, on the basis of the differences in coloration, of the C. albicans species from, on the one hand, the C. guilliermondii, C. kefyr, C. lusitaniae and/or C. tropicalis species, and, on the other hand, from the other Candida species, and of the C. guilliermondii, C. kefyr, C. lusitaniae and/or C. tropicalis species from the other Candida species.

When the medium contains no activator or inhibitor, a waiting period of between 36 and 60 hours and advantageously essentially 48 hours is allowed.

When the medium contains an activator or an inhibitor, a waiting period of between 18 and 30 hours and advantageously essentially 24 hours is allowed.

According to a first embodiment, these processes make it possible to identify C. albicans, C. guilliermondii, C. kefyr, C. lusitaniae and/or C. tropicalis from other Candida species, when the medium contains:

a hexosaminidase substrate, and/or a glucosidase substrate, and/or a hexosaminidase activator, and/or a hexosaminidase inhibitor.

According to a second embodiment, these processes make it possible to identify C. albicans from C. guilliermondii, C. kefyr, C. lusitaniae, C. tropicalis and/or other Candida species, when the medium contains:

a hexosaminidase substrate and a glucosidase substrate, and/or a hexosaminidase activator, and/or a hexosaminidase inhibitor.

The expression "compound which selectively inhibits the hexosaminidase activity of C. tropicalis" means any compound capable of selectively inhibiting the hexosaminidase activity of C. tropicalis. For example, the compounds of amide type of the formula described above have the property of specifically inhibiting the hexosaminidase activity of C. tropicalis without affecting that of C. albicans.

The term "identification" means detection and/or quantification.

The term "sample" in particular means any sample of biological type taken, a yeast strain or a set of yeast strains isolated, for example, after culturing.

The composition of the culture medium, expressed in g/l of final medium, is outlined below in general terms.

The medium comprises a nutrient base required for the growth of yeasts and inhibitors specific for the hexosaminidase of C. tropicalis according to the invention.

The constituent elements of the nutrient base comprise:

from 0.01 to 40 g/l of peptones, such as meat peptone, the product sold by the company bioMérieux under the brand name bioSoyase or the like, or alternatively a mixture of peptones; preferably, the peptone or the mixture of peptones is present in the medium at a concentration of about 6 g/l±0.5 g/l;

from 0.01 to 40 g/l, preferably about 1.5 g/l, of a yeast extract, supplying vitamins for the growth of the yeasts;

a source of carbon, such as glucose, glycerol, an acetate, a pyruvate, a lactate, arginine, an aminobutyrate or a mixture of these components, in a proportion of from 0 to 10 g/l; the carbon source is preferably glucose in an amount of 1 g/l;

a buffer added to the medium to give a pH which is favorable for the growth of C. albicans, of between 5 and 8.5; the buffer is chosen from phosphate buffer, Tris buffer, Hepes (N-2-hydroxyethylpiperazine-N'-2-ethanesulfonic acid) buffer and citrate buffer, in a proportion of from 2.5 to 100 mM; preferably, the buffer is a 10 mM phosphate buffer to adjust the pH of the medium to a value in the region of 7;

from 11 to 20 g/l, preferably 15 g/l, of agar.

The chromogenic or fluorigenic substrate can be any chromogenic or fluorigenic substrate which can be hydrolyzed with a hexosaminidase, such as a galactosaminidase, glucosaminidase or mannosaminidase, to release a colored or fluorescent product. Preferably, the substrate is chosen from those showing strong coloration or fluorescence with few molecules, and inducing no change in the metabolism of the microorganisms, except for the desired enzymatic activity. These substrates are preferably chosen, for the chromogenic substrates, from those comprising a chromophoric group such as a substituted or unsubstituted indolyl, and in particular from 5-bromo-4-chloro-3-indolyl-N-acetyl-β-D-glucosaminide, 5-bromo-4-chloro-3-indolyl-N-acetyl-β-D-galactosaminide, 6-chloro-3-indolyl-N-acetyl-β-D-glucosaminide and 5-bromo-6-chloro-3-indolyl-N-acetyl-β-D-glucosaminide of from 20 to 600 mM, advantageously 200 mM 5-bromo-4-chloro-3-indolyl-N-acetyl-β-D-glucosaminide, and for the fluorigenic substrates, from 4-methylumbelliferyl-N-acetyl-b-D-galactosaminide and 4-methylumbelliferyl-N-acetyl-b-D-glucosaminide.

The inhibitor which is specific for the hexosaminidase of yeasts of the *C. tropicalis* species is preferably chosen from the group of compounds of amide type (I) or mixtures thereof. It is chosen in particular from amides such as formamide, acetamide, propionamide, glycinamide, succinamide and the like. The amount of compound of amide type is between 0.01 and 20 g/l. Preferably, the inhibitor chosen is 1 g/l acetamide.

In order to obtain an intense and early activity for the yeasts of the *C. albicans* species, a hexosaminidase activator can advantageously be added to the culture medium, as described in document FR-A-2 684 110. Similarly, a bacterial inhibitor or a mixture of bacterial inhibitors, for inhibiting the growth of Gram-positive bacteria and that of Gram-negative bacteria, without affecting the growth of the yeasts, and if possible of fungi, can be added to the medium. Preferably, the bacterial inhibitors are chosen from the group of antibiotics such as gentamycin, chloramphenicol, penicillin, streptomycin, cycloheximide, neomycin, tetracycline, oxytetracycline or a mixture of antibiotics, and/or from tellurite, a molybdate and the like, or mixtures thereof. Advantageously, chloramphenicol (0.5 g/l) or a mixture of gentamycin (0.1 g/l) and chloramphenicol (0.05 g/l) is chosen. It is also possible to inhibit the growth of the bacteria by reducing the pH of the medium to an acidic pH.

As is demonstrated in the examples below, the enzymatic hydrolysis reaction remains specific beyond the 24 hours of incubation.

EXAMPLE 1

Tests were carried out to examine the effect of acetamide on the hexosaminidase activity of yeasts.

Two media were prepared according to the usual techniques. The first medium below, referred to as Medium I, contains all the elements of the nutrient base, as well as a chromogenic substrate for a hexosaminidase and a bacterial inhibitor mixture.

The composition of Medium I, per liter of final medium, is as follows:

| | |
|---|---|
| bioSoyase (bioMérieux) | 6.0 g |
| yeast extract (bioMérieux) | 1.5 g |
| glucose (Merck) | 1.0 g |
| phosphate buffer (Merck) | 10.0 mM |
| Mn2+ (Merck) | 1.0 mM |
| 5-bromo-4-chloro-3-indolyl-N-acetyl-β-D-glucosaminide (Biosynth) | 0.1 g |
| gentamycin | 0.1 g |
| chloramphenicol | 0.05 g |
| agar (bioMérieux) | 15.0 g |

The pH of the medium was adjusted to about 7.

The second medium, referred to as Medium II, corresponds to the medium according to the invention and contains all the elements described above for Medium I, plus the inhibitor which is specific for the hexosaminidase of *C. tropicalis*, i.e. an acetamide compound (Sigma) at 1.0 g.

12 strains of yeast were cultured directly in a Petri dish on these two media. The strains from the Applicant's collection belong to the following species: *C. albicans* (3 strains), *C. glabrata* (2 strains), *C. krusei* (1 strain), *C. parapsilosis* (1 strain), *C. tropicalis* (3 strains), *Saccharomyces cerevisiae* (1 strain), *Trichosporon* spp. (1 strain). The dishes were incubated at 37° C. for 48 hours. The colonies formed were examined visually, after incubation for 24 and 48 hours, respectively, according to the following interpretations:

the blue colonies correspond to strains producing N-acetyl-β-D-glucosaminidase, belonging in principle to the species *C. albicans;* the white colonies correspond to strains not producing the abovementioned enzyme or strains in which this enzyme is inhibited by the compound of amide type, these colonies thus belonging to other yeast strains, which will in this case be identified using the usual techniques.

The results are given in Table I below:

TABLE I

| | | Coloration | | | | | |
|---|---|---|---|---|---|---|---|
| | | at 24 hours | | | at 48 hours | | |
| Species | Medium | Strong | Weak | None | Strong | Weak | None |
| C. albicans | I | 1+ | 2 | — | 3 | — | — |
| | II | 1 | 2 | — | 3 | — | — |
| C. glabrata | I | — | — | 2 | — | — | 2 |
| | II | — | — | 2 | — | — | 2 |
| C. krusei | I | — | — | 1 | — | — | 1 |
| | II | — | — | 1 | — | — | 1 |
| C. parapsilosis | I | — | — | 1 | — | — | 1 |
| | II | — | — | 1 | — | — | 1 |
| C. tropicalis | I | — | — | 3 | 3 | — | — |
| | II | — | — | 3 | — | 1 | 2 |
| S. cerevisiae | I | — | — | 1 | — | — | 1 |
| | II | — | — | 1 | — | — | 1 |
| Trichosporon | I | — | — | 1 | 1 | — | — |
| | II | — | — | 1 | 1 | — | — |

+number of strains, "—" = 0

As emerges from Table I above, supplying the compound of amide type allows a specific detection of the *C. albicans* strains, since only the *C. albicans* strains, as well as one strain of *Trichosporon* after incubation for only 48 hours, produce colored colonies on the medium according to the invention. The *C. tropicalis* colonies which are blue after 48 hours on Medium I give colorless colonies on Medium II, apart from a very faint coloration after incubation for 48 hours.

EXAMPLE 2

The experiment of Example 1 was repeated, but using liquid media instead of gelled media. Media III and IV thus correspond to Media I and II of Example 1, but contain no agar. Moreover, the concentration of 5-bromo-4-chloro-3-indolyl-N-acetyl-b-D-glucosaminide is 150 mg/l of final medium for a use in liquid medium. The media were distributed into glass ampules, at a rate of 3 ml per ampule. The strains studied are the same as in Example 1. A suspension calibrated to 2 on the MacFarland scale using a nephelometer was prepared for each of the strains directly in the ampules containing the media. The ampules thus inoculated were incubated for 48 hours at 37° C. They were examined after 24 and 48 hours, respectively, according to the interpretations of Example 1.

The results are given in Table II below:

TABLE II

| | | Coloration | | | | | |
|---|---|---|---|---|---|---|---|
| | | at 24 hours | | | at 48 hours | | |
| Species | Medium | Strong | Weak | None | Strong | Weak | None |
| C. albicans | III | 1+ | 2 | — | 3 | — | — |
| | IV | 1 | 2 | — | 3 | — | — |
| C. glabrata | III | — | — | 2 | — | — | 2 |
| | IV | — | — | 2 | — | — | 2 |
| C. krusei | III | — | — | 1 | — | — | 1 |
| | IV | — | — | 1 | — | — | 1 |
| C. parapsilosis | III | — | — | 1 | — | — | 1 |
| | IV | — | — | 1 | — | — | 1 |
| C. tropicalis | III | — | 2 | 1 | 3 | — | — |
| | IV | — | — | 3 | — | 2 | 1 |
| S. cerevisiae | III | — | — | 1 | — | — | 1 |
| | IV | — | — | 1 | — | — | 1 |
| Trichosporon | III | — | — | 1 | — | 1 | — |
| | IV | — | — | 1 | — | 1 | — |

+number of strains, "—" = 0

As emerges from Table II above, supplying the amide compound allows a specific detection of the C. albicans strains. Specifically, after incubation for 24 hours, only the C. albicans strains give tubes colored blue in the medium according to the invention. The C. tropicalis strains, which give colored tubes in Medium III, give colorless tubes in Medium IV. After incubation for 48 hours, the coloration of the tubes containing C. tropicalis strains is also inhibited or at least very greatly reduced.

EXAMPLE 3

Tests were carried out to examine the effect of acetamide on the hexosaminidase activity of yeasts in the presence of an activator which is specific for this enzyme.

The experiment of Example 1 was reproduced, but with N-acetylglucosamine added to the medium. Media V and VI thus correspond to Media I and II of Example 1, to which N-acetylglucosamine has been added to a concentration of 1.0 g/l of final medium. The strains studied are the same as in Example 1. They were cultured directly in Petri dishes. The dishes were incubated at 37° C. for 48 hours. The colonies formed were examined visually, after incubation for 24 and 48 hours, respectively, according to the interpretations of Example 1.

The results are given in Table III below:

TABLE III

| | | Coloration | | | | | |
|---|---|---|---|---|---|---|---|
| | | at 24 hours | | | at 48 hours | | |
| Species | Medium | Strong | Weak | None | Strong | Weak | None |
| C. albicans | V | 2+ | 1 | — | 3 | — | — |
| | VI | 2 | 1 | — | 3 | — | — |
| C. glabrata | V | — | — | 2 | — | — | 2 |
| | VI | — | — | 2 | — | — | 2 |
| C. krusei | V | — | — | 1 | — | — | 1 |
| | VI | — | — | 1 | — | — | 1 |
| C. parapsilosis | V | — | — | 1 | — | — | 1 |
| | VI | — | — | 1 | — | — | 1 |
| C. tropicalis | V | — | — | 3 | 3 | — | — |
| | VI | — | — | 3 | — | — | 3 |

TABLE III-continued

| | | Coloration | | | | | |
|---|---|---|---|---|---|---|---|
| | | at 24 hours | | | at 48 hours | | |
| Species | Medium | Strong | Weak | None | Strong | Weak | None |
| S. cerevisiae | V | — | — | 1 | — | — | 1 |
| | VI | — | — | 1 | — | — | 1 |
| Trichosporon | V | — | — | 1 | 1 | — | — |
| | VI | — | — | 1 | 1 | — | — |

+number of strains, "—" = 0

As emerges from Table III above, supplying the compound of amide type allows a specific detection of the C. albicans strains. Specifically, only the C. albicans strains, as well as one strain of Trichosporon after incubation for 48 hours only, produce colored colonies on the medium according to the invention. The C. tropicalis strains which are blue on Medium V give colorless colonies on Medium VI. These two media together thus also allow a specific identification of yeasts of the C. tropicalis species, since, after incubation for 48 hours, they are the only ones which are positive on Medium V and negative on Medium VI.

EXAMPLE 4

Tests were carried out to examine the effect of a mixture of amide compounds on the hexosaminidase activity of yeasts in the presence of an activator which is specific for this enzyme.

The experiments of Example 3 was reproduced, but with formamide at a concentration of 0.5 g/l of final medium (Medium VIII) being added to Medium VII, Medium VII being identical to Medium V of Example 3. The strains studied are the same as those in Example 3. They were cultured directly in Petri dishes. The dishes were incubated at 37° C. for 48 hours. The colonies formed were examined visually, after incubation for 24 and 48 hours, respectively, according to the interpretations of Example 1.

The results are given in Table IV below:

TABLE IV

| | | Coloration | | | | | |
|---|---|---|---|---|---|---|---|
| | | at 24 hours | | | at 48 hours | | |
| Species | Medium | Strong | Weak | None | Strong | Weak | None |
| C. albicans | VII | 2+ | 1 | — | 3 | — | — |
| | VIII | 2 | 1 | — | 3 | — | — |
| C. glabrata | VII | — | — | 2 | — | — | 2 |
| | VIII | — | — | 2 | — | — | 2 |
| C. krusei | VII | — | — | 1 | — | — | 1 |
| | VIII | — | — | 1 | — | — | 1 |
| C. parapsilosis | VII | — | — | 1 | — | — | 1 |
| | VIII | — | — | 1 | — | — | 1 |
| C. tropicalis | VII | — | — | 3 | 3 | — | — |
| | VIII | — | — | 3 | — | — | 3 |
| S. cerevisiae | VII | — | — | 1 | — | — | 1 |
| | VIII | — | — | 1 | — | — | 1 |
| Trichosporon | VII | — | — | 1 | 1 | — | — |
| | VIII | — | — | 1 | — | 1 | — |

+number of strains, "—" = 0

As emerges from Table IV above, supplying a second compound of amide type allows an even more specific detection of the C. albicans strains, since only the C. albicans strains produce colonies that are significantly colored on the medium according to the invention. The C.

*tropicalis* strains which are blue on Medium VII give colorless colonies on Medium VIII, and the *Trichosporon* strain which is highly colored after incubation for 48 hours on Medium VII is only very faintly colored on Medium VIII.

EXAMPLE 5

Tests were carried out to examine the advantage of combining a hexosaminidase substrate and a β-glucosidase substrate in media for isolating and identifying yeasts.

A β-glucosidase substrate, 6-chloro-3-indolyl-β-D-glucoside, was added at a concentration of 0.07 g/l to Medium I of Example 1 (Medium IX). To this medium was added either a hexosaminidase activator (N-acetyl-glucosamine) at 1 g/l (Medium X), or an inhibitor of the hexosaminidase of *C. tropicalis* (acetamide) at 1 g/l (Medium XI), or a combination of the abovementioned activator and inhibitor at the same concentrations (Medium XII).

Eighteen strains of yeast were cultured directly in Petri dishes on these four media. The strains from the Applicant's collection belong to the following species: *C. albicans* (3 strains), *C. glabrata* (2 strains), *C. guilliermondii* (2 strains), *C. kefyr* (2 strains), *C. krusei* (1 strain), *C. lusitaniae* (2 strains), *C. parapsilosis* (1 strain), *C. tropicalis* (3 strains), *Saccharomyces cerevisiae* (1 strain), *Trichosporon* spp. (1 strain). The dishes were incubated at 37° C. for 48 hours. The colonies formed were examined visually, after incubation for 24 and 48 hours, respectively, according to the following interpretations:

- the blue colonies correspond to strains producing N-acetyl-β-D-glucosaminidase, belonging in principle to the *C. albicans* species;
- the pink colonies correspond to strains producing β-D-glucosidase, belonging in principle to the *C. guilliermondii*, *C. kefyr*, *C. lusitaniae* and *C. tropicalis* species;
- the mauve colonies correspond to strains producing the two enzymatic activities;
- the white colonies correspond to strains producing none of the abovementioned enzymes or to strains in which these enzymes are inhibited, and they thus belong to other yeast species which will in this case be identified using the usual techniques.

The results are given in Table V below:

TABLE V

| Species | Me-dium | Coloration at 24 hours | | | Coloration at 48 hours | | |
|---|---|---|---|---|---|---|---|
| | | Strong | Weak | None | Strong | Weak | None |
| C. albicans | IX | 1-blue | 2-blue | — | 3-blue | — | — |
| | X | 2-blue | 1-blue | — | 3-blue | — | — |
| | XI | 1-blue | 2-blue | — | 3-blue | — | — |
| | XII | 2-blue | 1-blue | — | 3-blue | — | — |
| C. glabrata | IX | — | — | 2 | — | — | 2 |
| | X | — | — | 2 | — | — | 2 |
| | XI | — | — | 2 | — | — | 2 |
| | XII | — | — | 2 | — | — | 2 |
| C. guil-liermondii | IX | — | — | 2 | 2-pink | — | 2 |
| | X | — | — | 2 | 2-pink | — | 2 |
| | XI | — | — | 2 | 2-pink | — | 2 |
| | XII | — | — | 2 | — | 2-pink | 2 |
| C. kefyr | IX | — | 2-pink | 2 | 2-pink | — | 2 |
| | X | — | 2-pink | 2 | 2-pink | — | 2 |

TABLE V-continued

| Species | Me-dium | Coloration at 24 hours | | | Coloration at 48 hours | | |
|---|---|---|---|---|---|---|---|
| | | Strong | Weak | None | Strong | Weak | None |
| | XI | — | 2-pink | 2 | 2-pink | — | 2 |
| | XII | — | 2-pink | 2 | 2-pink | — | 2 |
| C. krusei | IX | — | — | 1 | — | — | 1 |
| | X | — | — | 1 | — | — | 1 |
| | XI | — | — | 1 | — | — | 1 |
| | XII | — | — | 1 | — | — | 1 |
| C. lusitaniae | IX | — | — | 2 | 1-pink | 1-pink | 2 |
| | X | — | — | 2 | 2-pink | — | 2 |
| | XI | — | — | 2 | 1-pink | 1-pink | 2 |
| | XII | — | — | 2 | 2-pink | — | 2 |
| C. parap-silosis | IX | — | — | 1 | — | — | 1 |
| | X | — | — | 1 | — | — | 1 |
| | XI | — | — | 1 | — | — | 1 |
| | XII | — | — | 1 | — | — | 1 |
| C. tropicalis | IX | 2-pink | 1-pink | — | 2-mauve | 1-pink | — |
| | X | 2-pink | 1-pink | — | 2-mauve | 1-pink | 3 |
| | XI | 2-pink | 1-pink | — | 3-pink | — | 3 |
| | XII | 2-pink | 1-pink | — | 3-pink | — | 3 |
| S. cerevisiae | IX | — | — | 1 | — | — | 1 |
| | X | — | — | 1 | — | — | 1 |
| | XI | — | — | 1 | — | — | 1 |
| | XII | — | — | 1 | — | — | 1 |
| Tricho-sporon | IX | — | — | 1 | 1 | — | — |
| | X | — | — | 1 | — | — | 1 |
| | XI | — | — | 1 | — | — | 1 |
| | XII | — | — | 1 | — | 1 | — |

+number of strains - color of colonies, "—" = 0

As emerges from Table V above, supplying a combination of a hexosaminidase substrate and a β-glucosidase substrate allows detection of a larger number of yeast species, since it is possible on the media according to the invention to distinguish the *C. albicans* strains, on the one hand, and the *C. guilliermondii*, *C. kefyr*, *C. lusitaniae* and *C. tropicalis* strains, on the other hand, from the other yeast species. Media X, XI and XII illustrate the advantage of combining this substrate combination with a hexosaminidase activator, with an inhibitor which is specific for the hexosaminidase of *C. tropicalis* strains or with a mixture of the two. On Medium X, the *C. albicans* strains are detected more quickly than on Medium IX; on Medium XI, the difference between the *C. albicans* strains and the *C. tropicalis* strains is more pronounced and Medium XII combines the advantages of Media X and XI.

What is claimed is:

1. A culture medium for the specific identification and/or differentiation of *Candida albicans* and *Candida tropicalis* yeast, comprising a chromogenic or fluorigenic substrate that can be hydrolyzed by an enzyme of the hexosaminidase family and an acetamide that selectively inhibits the hexosaminidase activity of *C. tropicalis*.

2. The medium according to claim 1, further comprising an activator specific for the hexosaminidase enzyme of *C. albicans*.

3. The medium according to claim 2, wherein the activator is N-acetylglucosamine.

4. The medium according to claim 1, further comprising formamide.

5. The medium according to claim 1, wherein the medium is gelled and comprises, per liter:

| | |
|---|---|
| peptones or a mixture of peptones | 0.01–40 g |
| yeast extract | 0.01–40 g |
| glucose (source of carbon) | 0–10 g |
| phosphate buffer (pH between 5 and 8.5) | 2.5–100 mM |
| 5-bromo-4-chloro-3-indolyl-N-acetyl-β-D-glucosaminide | 20–600 × $10^{-6}$ M |
| acetamide | 0.01–20 g |
| bacterial inhibitor | 0–20 g |
| agar | 11–20 g. |

6. The medium according to claim 5, further comprising N-acetylglucosamine at a concentration of 1.0 g/l.

7. The medium according to claim 5, further comprising formamide at a concentration of 0.5 g/l.

8. Microbiological analysis process for detecting and selectively identifying certain species of *Candida* yeast, comprising:
  placing a sample in direct contact with a culture medium comprising two substrates, a first chromogenic or fluorigenic substrate that can be hydrolyzed by an enzyme from the hexosaminidase family, and a second chromogenic or fluorigenic substrate that can be hydrolyzed by an enzyme from the glucosidase family;
  allowing time for colorations to appear in the medium; and
  identifying, on the basis of the differences in coloration, *C. albicans* species from *C. guilliermondii, C. kefyr, C. lusitaniae* and/or *C. tropicalis* species, *C. albicans* species from other *Candida* species, and/or *C. guilliermondii, C. kefyr, C. lusitaniae* and/or *C. tropicalis* species from other *Candida* species.

9. The process according to claim 8, wherein said culture medium further comprises a hexosaminidase activator and/or a hexosaminidase inhibitor.

10. The process according to claim 9, wherein a waiting period of at least 18 hours is allowed.

11. The process according to claim 10, wherein a waiting period of between 18 and 30 hours is allowed.

12. The process according to claim 11, wherein a waiting period of 24 hours is allowed.

13. The process according to claim 8, wherein a waiting period of at least 36 hours is allowed when the medium contains no hexosaminidase activator or hexosaminidase inhibitor.

14. The process according to claim 13, wherein a waiting period of between 36 and 60 hours is allowed.

15. The process according to claim 14, wherein a waiting period of 48 hours is allowed.

16. The process according to claim 8, said process comprising identifying *C. albicans* species from *C. guilliermondii, C. kefyr, C. lusitaniae* and/or *C. tropicalis* species.

17. The process according to claim 8, said process comprising identifying *C. albicans, C. guilliermondii, C. kefyr, C. lusitaniae* and/or *C. tropicalis* species from other Candida species.

18. The process according to claim 9, said culture medium comprising a hexosaminidase inhibitor that is an acetamide.

19. The process according to claim 18, said culture medium further comprising formamide.

20. The process according to claim 9, said culture medium comprising a hexosaminidase activator that is N-acetylglucosamine.

* * * * *